United States Patent
Cintrat et al.

(10) Patent No.: US 12,024,508 B2
(45) Date of Patent: Jul. 2, 2024

(54) DIHYDROQUINAZOLINONES EXHIBITING PROTECTIVE ACTIVITY AGAINST INTRACELLULAR-ACTING TOXINS, INTRACELLULAR VIRUSES AND BACTERIA

(71) Applicant: Commissariat a l'Energie Atomique et aux Energies Alternatives, Paris (FR)

(72) Inventors: Jean-Christophe Cintrat, Igny (FR); Julien Barbier, Gif-sur-Yvette (FR); Daniel Gillet, Antony (FR); Alain Pruvost, Choisel (FR); Audrey Couhert, Villefontaine (FR); Livia Tepshi, Antony (FR); Robin Vinck, Gif-sur-Yvette (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 608 days.

(21) Appl. No.: 17/296,612

(22) PCT Filed: Nov. 28, 2019

(86) PCT No.: PCT/EP2019/082976
§ 371 (c)(1),
(2) Date: May 25, 2021

(87) PCT Pub. No.: WO2020/109510
PCT Pub. Date: Jun. 4, 2020

(65) Prior Publication Data
US 2022/0002289 A1    Jan. 6, 2022

(30) Foreign Application Priority Data

Nov. 28, 2018 (FR) ...................................... 1872016

(51) Int. Cl.
*C07D 417/14* (2006.01)
*A61K 47/59* (2017.01)
*A61K 47/60* (2017.01)

(52) U.S. Cl.
CPC .......... *C07D 417/14* (2013.01); *A61K 47/593* (2017.08); *A61K 47/60* (2017.08)

(58) Field of Classification Search
None
See application file for complete search history.

(56) References Cited

U.S. PATENT DOCUMENTS 9,598,406 B2 * 3/2017 Gillet .................... A61K 31/517

FOREIGN PATENT DOCUMENTS

| EP | 2722047 A1 | 4/2014 |
| EP | 2722328 A1 | 4/2014 |
| EP | 3085374 A1 | 10/2016 |

OTHER PUBLICATIONS

Noel et al., "N-Methyldihydroquinazolinone Derivatives of Retro-2 with Enhanced Efficacy against Shiga Toxin," Journal of Medicinal Chemistry, 56 (8): 3404-3413 (2013).
(Continued)

*Primary Examiner* — Karl J Puttlitz
(74) *Attorney, Agent, or Firm* — Morgan, Lewis & Bockius LLP

(57) ABSTRACT

The invention relates to a new family of compounds of the type 2,3-dihydroquinazolin-4(1H)-one and the use thereof as inhibitors of the toxic effects of intracellular-acting toxins, such as ricin, Shiga toxins or the cholera toxin, using retrograde transport to intoxicate the cells, or viruses or bacteria using retrograde and/or syntaxin 5-dependent transport to infect the cells, specifically viruses or bacteria entering into the cells by means of endocytosis, or intracellular parasites.

17 Claims, 2 Drawing Sheets

(56) References Cited

OTHER PUBLICATIONS

Lord et al., "Retrograde transport of toxins across the endoplasmic reticulum membrane," Biochemical Society Transactions, 31 (6): 1260-1262 (2003).
Gupta et al., "(S)-N-Methyldihydroquinazolinones are the Active Enantiomers of Retro-2 Derived Compounds against Toxins," ACS Medicinal Chemistry Letters, (2013).
International Search Report issued in corresponding International Patent Application No. PCT/EP2019/082976 dated May 18, 2020.

* cited by examiner

DIHYDROQUINAZOLINONES EXHIBITING PROTECTIVE ACTIVITY AGAINST INTRACELLULAR-ACTING TOXINS, INTRACELLULAR VIRUSES AND BACTERIA

The present invention relates to a new family of 2,3-dihydroquinazolin-4(1H)-one compounds and their use as inhibitors of the toxic effects of the intracellular-acting toxins, such as the ricin, the Shiga toxins and the cholera toxin, using retrograde transport to intoxicate the cells, or viruses or bacteria using retrograde and/or syntaxin 5-dependent transport to infect the cells, including the viruses or bacteria entering the cells by endocytosis, or intracellular parasites.

The intracellular-acting toxins that use the retrograde transport represent a major public health risk, some of which are associated with more than one million deaths worldwide each year. These toxins comprise in particular the ricin (produced in the seeds of the plant *Ricinus communis*), the Shiga toxin and the Shiga-like toxins (Stxs) produced by *Shigella dysenteriae* (Stx) and *E. coli* (Stx1 and Stx2), the cholera toxin (Ctx from *Vibrio cholerae* responsible for cholera), the pertussis toxin (*Bordetella pertussis* agent of whooping cough), the subtilase cytotoxin and the heat-labile enterotoxin (*E. coli*).

The ricin is a 66 kDa glycoprotein composed of two polypeptide chains connected by a disulphide bridge (FIG. 1A). The B-chain (RTB, 262 residue lectin) allows the toxin to bind to the glycolipids and glycoproteins of the cell membranes and ensure its entry into the cell (FIG. 1A). The A-chain (RTA, 267 amino acids) ensures the N-glycosidase enzyme function of the ricin, catalyses the removal of the 4324 adenine from the 28S RNA of the target cells and causes the synthesis of the proteins to be stopped.

The Shiga toxins comprise the Shiga toxin (Stx) produced by *Shigella dysenteriae* and the Shiga-like toxins 1 (Stx1) and 2 (Stx2) produced by enterohemorrhagic strains of *E. coli*. The Stx and Stx1 toxins are 99% identical whereas the Stx1 and Stx2 share only 56% of identity of their amino acid sequence. The A subunit of the toxin (StxA) carries the same enzymatic activity as the ricin and targets the 28S RNA in an identical manner (FIG. 1B). The B subunit (StxB), which is pentameric, allows the binding of the toxin to the cell via its interaction with the globo-triaosylceramide Gb3, thus ensuring its internalisation and its intracellular routing.

After binding to its membrane receptors, the ricin is internalised in these cells through multiple endocytosis pathways to reach the trans-golgiate network where it is delivered to the endoplasmic reticulum (ER) by retrograde transport (Johannes, L. et al., *Cell* 2008, 135, 1175-87). The Shiga toxins are internalised by a unique endocytosis pathway and also reach the Golgi apparatus and then the endoplasmic reticulum (ibid.).

The toxins are then partially unfolded and the chain/subunit A is translocated into the cytosol (Lord, J. M. et al., *Biochemical Society Transactions* 2003, 31, 1260). The final step in the action of these toxins therefore takes place in the cytoplasm of the cells, the toxins bind to the ribosomes with great efficiency and cleave the adenine 4324 of the 28S RNA of the subunit 60S of the ribosome. This depurination of the 28S RNA causes the protein synthesis to stop and leads to the cell death.

To counter the threat posed by these toxins, several types of antitoxins have been developed: neutralising antibodies, inhibitors of the enzymatic activity (small molecules, substrate analogues), soluble receptor mimics and chemical compounds acting on the cells targeted by the toxin.

In recent years, the search for new molecules to block the intracellular routing of the intracellular-acting toxins has accelerated. The main advantage of such molecules is their broad-spectrum activity, as these molecules can effectively protect the cells against the different toxins that use the retrograde pathway.

In the context of its research on compounds blocking the retrograde transport and more particularly studies on compounds more advantageous than those of the above mentioned work, the Applicant has identified a new family of compounds derived from 2,3-dihydroquinazolin-4(1H)-one, bearing a specifically substituted phenyl in the ortho or meta position, which unexpectedly exhibit a biological activity superior to that of Retro-2.1, the most active of the molecules already described, and therefore of marked interest for the prevention and/or the treatment of intoxications to at least one intracellular-acting toxin using retrograde transport to infect the mammalian eukaryotic cells, but also for the prevention and/or the treatment of the infections by viruses or bacteria using retrograde and/or syntaxin 5-dependent transport to infect cells, in particular the viruses or bacteria entering into the cells by endocytosis, or to intracellular parasites.

Thus, the present invention relates to a compound of general formula (I):

where:
p is equal to 1, 2 or 3;
$R_1$ represents at each occurrence, independently, a hydrogen atom, a halogen atom, an alkoxy radical of 1 to 3 carbon atoms, in particular a methoxy group, $-NO_2$, or $-NH_2$;
$R_2$ and $R_3$ independently of each other represent a group selected from H, $-OH$, $-OR_4$, $-NH_2$, $-NHR_5$, $-SO_2-NH_2$, $-SO_2-NH-R_6$, provided that at least one of $R_2$ and $R_3$ does not represent H;
$R_4$, $R_5$ and $R_6$ independently of each other represent a group of formula (II) $-L-(X)_i-(PEG)-(Y)_j-Z$, wherein:
i and j independently of each other represent 0 or 1;
L represent $-C(=O)-$ or $-C(=O)-(CH_2)_k-C(=O)-$, where k is equal to 1, 2 or 3, in particular 2;
X and Y independently of each other represent poly(lactic acid) or poly(lactic acid-co-glycolic acid);
PEG represents a poly(ethylene glycol);
Z represents a group selected from H, a $C_1$ to $C_3$ alkyl, $-OH$, a $O-C_1$ to $C_3$ alkyl, or $-L-R_e$, wherein L is defined as above and $R_e$ is a residue of formula (I) linked to said $-L-(X)_i-(PEG)-(Y)_j-$ group defined above via its $R_2$ or $R_3$ group, said $R_2$ or $R_3$ group being —OH, —NH$_2$ or —SO$_2$—NH$_2$;

as well as the stereoisomeric forms, the mixtures of stereoisomeric forms or their pharmaceutically acceptable salts.

The present invention also relates to a compound of general formula (I):

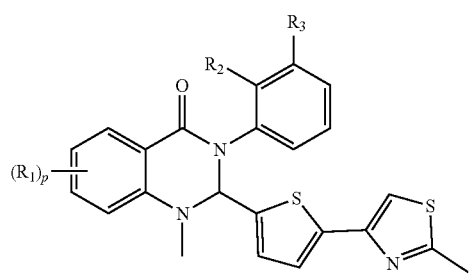

(I)

wherein:

p is equal to 1, 2 or 3;

$R_1$ represents at each occurrence, independently, a hydrogen atom, a halogen atom or an alkoxy radical of 1 to 3 carbon atoms, in particular a methoxy group;

$R_2$ and $R_3$ represent, independently of each other, a group selected from H, —OH, —NH$_2$, —SO$_2$—NH$_2$, on the condition that at least one of $R_2$ and $R_3$ does not represent H;

as well as the stereoisomeric forms, the mixtures of stereoisomeric forms or their pharmaceutically acceptable salts.

According to an embodiment, $R_2$ represents a group selected from —OH, —NH$_2$, —SO$_2$—NH$_2$, and $R_3$ represents a group selected from H, —OH, —NH$_2$, —SO$_2$—NH$_2$.

According to an embodiment, $R_3$ represents a hydrogen atom. The compound of general formula (I) according to the invention is then of the following formula:

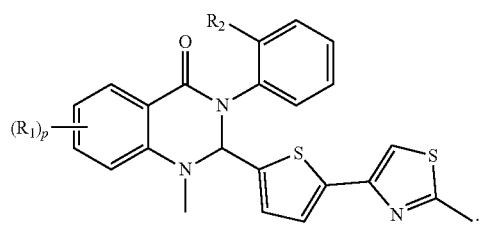

According to an embodiment $R_2$ represents a hydrogen atom. The compound of general formula (I) according to the invention is then of the following formula:

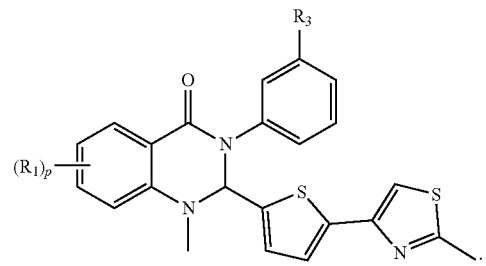

According to an embodiment, $R_2$ and $R_3$ represent, independently of each other, a group selected from —OH, —NH$_2$, —SO$_2$—NH$_2$, $R_2$ and $R_3$ representing in particular —OH.

According to an embodiment, p is equal to 1.

According to an embodiment, the compound of general formula (I) according to the invention is of the following formula:

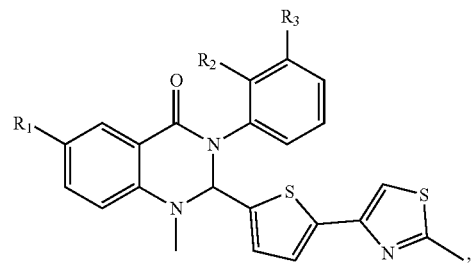

$R_1$, $R_2$ and $R_3$ being as defined above, $R_2$ and $R_3$ representing in particular, independently of each other, a group selected from —OH, —NH$_2$, —SO$_2$—NH$_2$, $R_2$ and $R_3$ representing for example —OH.

According to a particular embodiment, the compound of general formula (I) according to the invention is of the following formula:

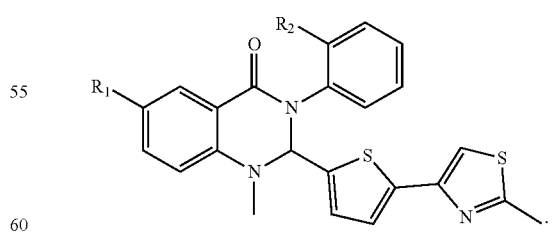

According to a particular embodiment, the compound of general formula (I) according to the invention is of the following formula:

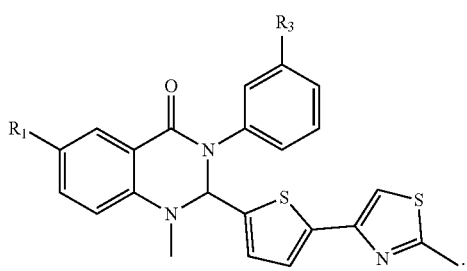

According to an embodiment, $R_1$ represents a halogen atom, in particular a fluorine atom.

According to a particular embodiment, the compound of general formula (I) according to the invention is of the following formula (Ia):

(Ia)

[structure Ia]

According to an embodiment, the compound of general formula (I) according to the invention is of the following formula (Ib):

(Ib)

[structure Ib]

According to an embodiment, the compound of general formula (I) according to the invention is selected from:

4
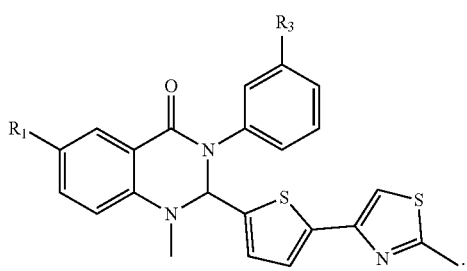

1
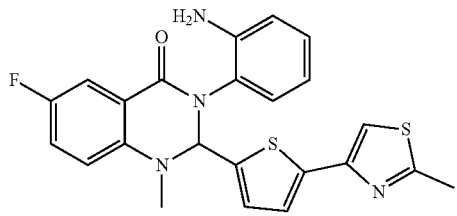

2
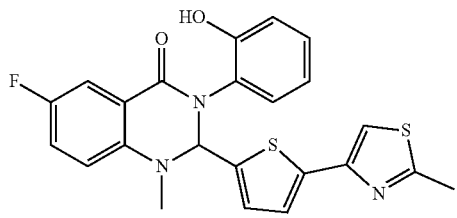

5
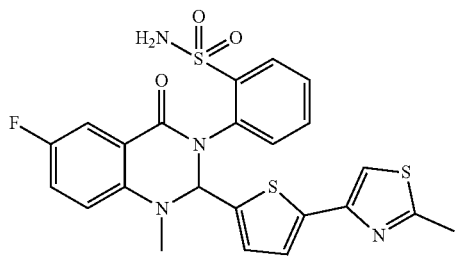

3
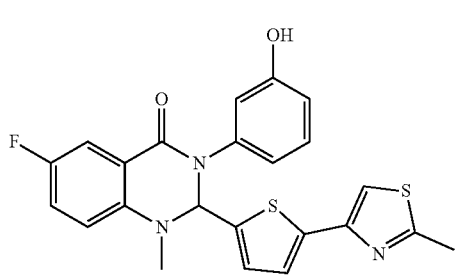

7
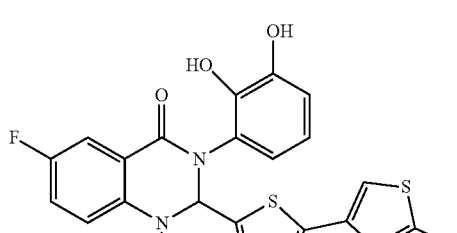

According to an embodiment, the invention relates to a compound of general formula (I) in which $R_2$ and $R_3$ represent, independently of each other, a group selected from H, —OH, —$OR_4$, —$NH_2$, —$NHR_5$, —$SO_2$—$NH_2$, —$SO_2$—NH—$R_6$, on the condition that at least one of $R_2$ and $R_3$, in particular $R_2$, represents a group selected from —$OR_4$, —$NHR_5$ and —$SO_2$—NH—$R_6$, $R_4$, $R_5$ and $R_6$ being defined as previously.

As regards the group of formula (II) -L-$(X)_i$-(PEG)-$(Y)_j$—Z, L represents in particular —C(=O)— when $R_2$ or $R_3$ represents —$NHR_5$ or —$SO_2$—NH—$R_6$, and L represents in particular -C(=O)—$(CH_2)_k$—C(=O)— when $R_2$ or $R_3$ represents —$OR_4$.

According to an embodiment, the group of formula (II) -L-$(X)_i$-(PEG)-$(Y)_j$—Z is selected from -L-PEG, -L-PEG-PLA, and -L-PLGA-PEG-PLGA, with L representing in particular —C(=O)— when R$_2$ or R$_3$ represents —NHR$_5$ or —SO$_2$—NH—R$_6$, or in particular —C(=O)—(CH$_2$)$_k$—C(=O)— when R$_2$ or R$_3$ represents —OR$_4$.

According to an embodiment, the group of formula (II) -L-(X)$_i$—(PEG)-(Y)$_j$—Z is selected from —C(=O)—(CH$_2$—CH$_2$—O)$_m$—CH$_3$, in particular when R$_2$ or R$_3$ represents —NHR$_5$ or —SO$_2$—NH—R$_6$, and —C(=O)—(CH$_2$)$_k$—C(=O)—(O—CH$_2$—CH$_2$)$_m$—OCH$_3$, in particular when R$_2$ or R$_3$ represents —OR$_4$, m being comprised from 1 to 500, for example from 4 to 500, m being comprised in particular from 30 to 60, more particularly 45.

According to an embodiment, the compound of general formula (I) is of the following formula (III):

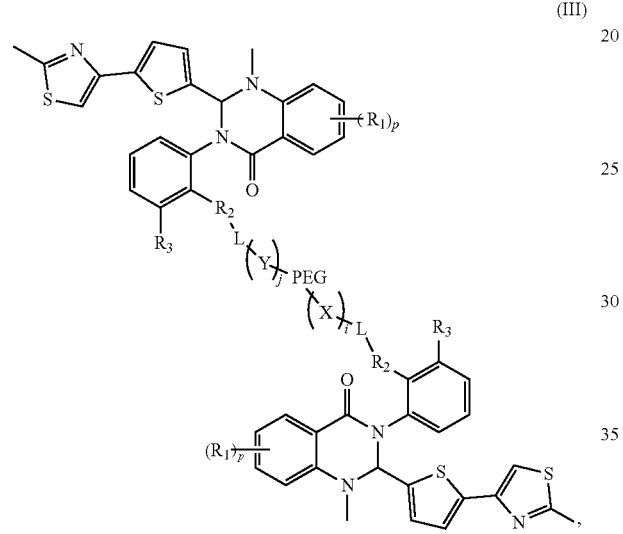

(III)

the groups mentioned in formula (III) being as defined above.

According to an embodiment, the compound of general formula (I) according to the invention is selected from:

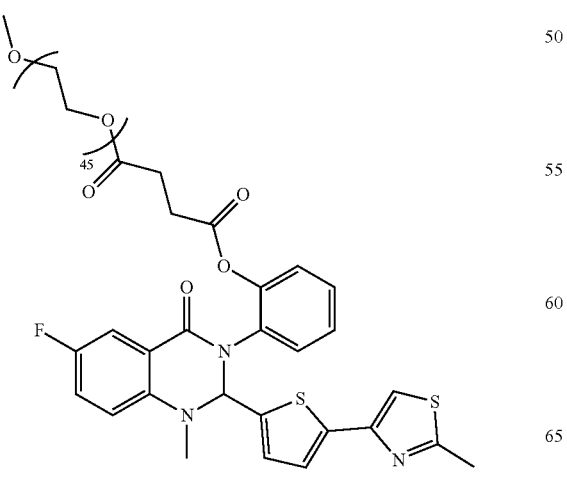

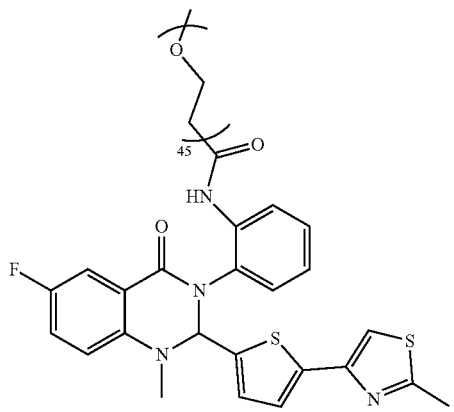

R = PEG$_{450}$
R = PEG-PLA
R = PLGA-PEG-PLGA
in particular PLGA$_{1036}$-PEG$_{1450}$-PLGA$_{1036}$

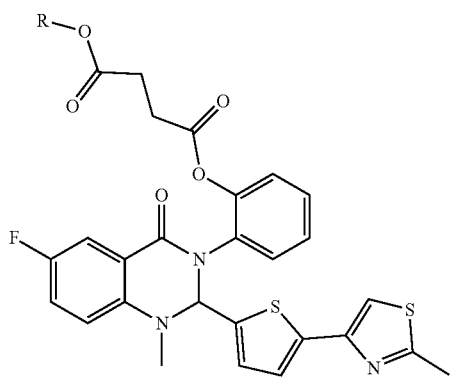

and (Compound 2)-PLGA1036-PEG1450-PLGA1036-(Compound 2) or (Compound 2)-C(=O)—(CH$_2$)$_2$—C(=O)—PLGA1036-PEG1450-PLGA1036-C(=O)—(CH$_2$)$_2$—C(=O)-(Compound 2), in particular of the following formula:

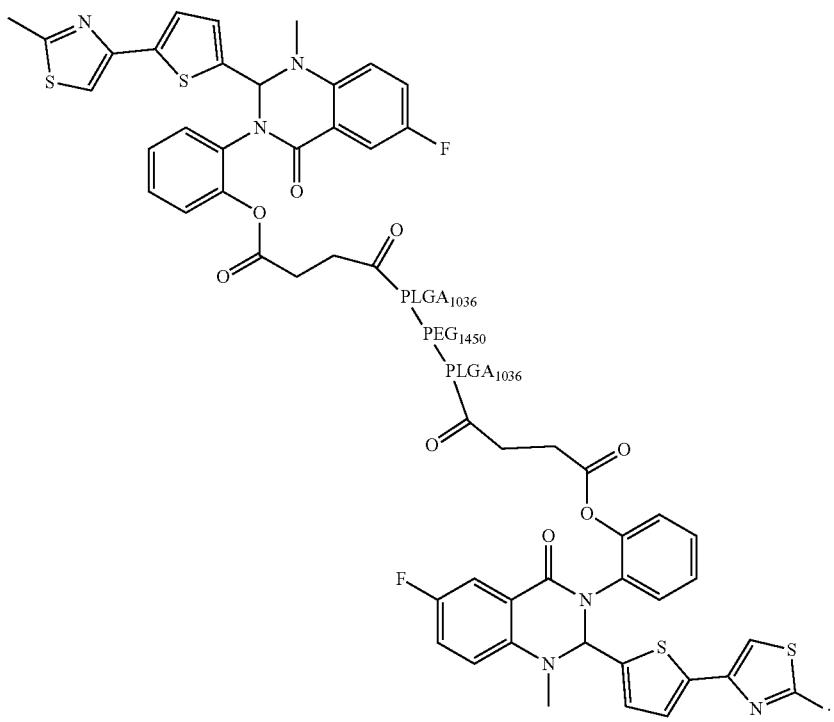

30

According to another aspect, the invention relates to a pharmaceutical composition or medicament comprising at least one compound of general formula (I) as defined above, as active principle, and a pharmaceutically acceptable carrier, said pharmaceutical composition or said medicament being suitable in particular for administration by the aerial, oral, parenteral or local routes.

It is to be noted that all the above-mentioned embodiments of the compound of general formula (I) also apply herein, alone or in combination.

According to another aspect, the invention relates to a compound of general formula (I) as defined above, for use in the prevention and/or treatment of the disorders induced by the intracellular-acting toxins using the retrograde transport, or by the viruses or bacteria using retrograde and/or syntaxin 5-dependent transport to infect the cells, in particular the viruses or bacteria entering the cells by endocytosis, or by intracellular parasites.

It should be noted that all the above-mentioned embodiments of the compound of general formula (I) also apply herein, alone or in combination.

According to an embodiment, the invention relates to a compound of general formula (I) as defined above, for use in the prevention and/or the treatment of the disorders induced by the intracellular-acting toxins using the retrograde transport.

According to a particular embodiment, said intracellular-acting toxins using the retrograde transport are selected from the ricin, the Shiga toxin and the Shiga-like toxins (Stxs) produced by *Shigella dysenteriae* (Stx) and *E. coli* (Stx1 and Stx2, Stx, Stx1a, Stx2a, Stx2c, Stx2d, Stx2e as described for example by Melton-Celsa, *Microbiol Spectr.* 2014; 2(2)), the cholera toxin (Ctx from *Vibrio cholerae* responsible for cholera), the pertussis toxin (*Bordetella pertussis* agent of whooping cough), the subtilase cytotoxin and the heat-labile enterotoxin (*E. coli*).

According to an embodiment, the invention relates to a compound of general formula (I) as defined above, for use in the prevention and/or the treatment of the disorders induced by the viruses or bacteria using retrograde and/or syntaxin 5-dependent transport to infect the cells, in particular the viruses or bacteria entering the cells by endocytosis, or the intracellular parasites.

According to a particular embodiment, the viruses are pox viruses, in particular the smallpox virus and the Vaccinia virus, the cytomegaloviruses, the adenoviruses, in particular the adeno-associated viruses, in particular of serotype 2, the polyomaviruses, in particular the JC polyomavirus and the BK polyomavirus, the papillomaviruses, the filoviruses, in particular the Ebola viruses and the Marburg virus, the enteroviruses, in particular the enterovirus 71, the herpes viruses, in particular the Herpes simplex virus type 2, the viruses of the *Arenavirus* genus, in particular the virus of the lymphocytic choriomeningitis, the influenza viruses, in particular the influenzaviruses A According to a particular embodiment, the viruses are the pox viruses, in particular the smallpox virus, the monkeypox virus, the Vaccinia virus and the leporipoxviruses, in particular the myxomatosis virus, the cytomegaloviruses, the adeno-associated viruses, in particular of serotype 2, the polyomaviruses, in particular the JC polyomavirus and the BK polyomavirus, the papillomaviruses, the filoviruses, in particular the Ebola viruses and the Marburg virus, the enteroviruses, in particular the enterovirus 71, the herpes viruses, in particular the Herpes simplex virus type 2, the viruses of the *Arenavirus* genus, in particular the lymphocytic choriomeningitis virus, the influenza viruses, in particular the influenzaviruses A, the pneumoviruses, in particular the respiratory syncytial virus.

According to a particular embodiment, the bacteria are bacteria of the order of the Chlamydiales, in particular of the genus *Chlamydia*, such as *Chlamydia trachomatis*, *Chla-

*mydophila pneumoniae, Chlamydophila psyttaci,* or *Symkania*, such as *Symkania negevensis*.

According to a particular embodiment, the disorders induced by the intracellular parasites are the leishmaniasis, in particular induced by trypanosomes of the genus *Leishmania*, in particular *Leishmania infantum, Leishmania donovani* or *Leishmania infantum/donovani* hybrid.

The present invention also relates to a method of preventing and/or treating the disorders induced by the intracellular-acting toxins using the retrograde transport and comprising the administration of an effective amount of at least one compound of general formula (I) as defined above.

It is to be noted that all the embodiments mentioned above with respect to the compound of general formula (I) also apply herein, alone or in combination.

Synthesis

The compounds of the present invention may be prepared by methods well known to the person skilled in the art, comprising, but not limited to, those described below, or by modifications of such methods by applying standard techniques known to the person skilled in the art in the organic synthesis. The suitable modifications and substitutions will be well known, easily apparent, or easily available from the scientific literature to the person skilled in the art. In particular, such methods can be found in R. C. *Larock, Comprehensive Organic Transformations,* Wiley-VCH Publishers, 1999.

All of the processes disclosed in the context of the present invention are contemplated to be practiced on any scale, including the milligram, the gram, the multigram, the kilogram, the multikilogram or the commercial industrial scale.

It should be noted that the compounds of the present invention may comprise an asymmetrically substituted carbon atom, and may be isolated in optically active or racemic forms. Thus, all the chiral, diastereomeric, racemic, isomeric forms of a structure are contemplated, unless the specific stereochemistry or isomeric form is specifically indicated. It is well known to prepare and isolate such optically active forms. For example, the mixtures of stereoisomers may be separated by standard techniques including, but not limited to, the resolution of racemic forms, the conventional chromatography, in reverse phase and chiral, the preferential salt formation, the recrystallization and the like, or by chiral synthesis from chiral raw materials or by deliberate synthesis of the target chiral centres.

The compounds of the present invention can be prepared by various synthetic pathways.

In the reactions described below, it may be necessary to protect the reactive functional groups, for example hydroxy, amino or thio groups, where these are present in the final product, in order to avoid their participation in secondary, unwanted reactions. The conventional protecting groups can be used according to common practice, for example, see T.W. Greene and P. G. M. Wuts in *Protective Groups in Organic Chemistry,* 3rd ed., John Wiley and Sons, 1999; J. F. W. McOmie in *Protective Groups in Organic Chemistry,* Plenum Press, 1973.

The reactive and the starting compounds are commercially available, or easily synthesised by techniques well known to the person skilled in the art. All the substituents, unless otherwise stated, are as previously defined.

The compounds of general formula (I) can be obtained according to the following reaction:

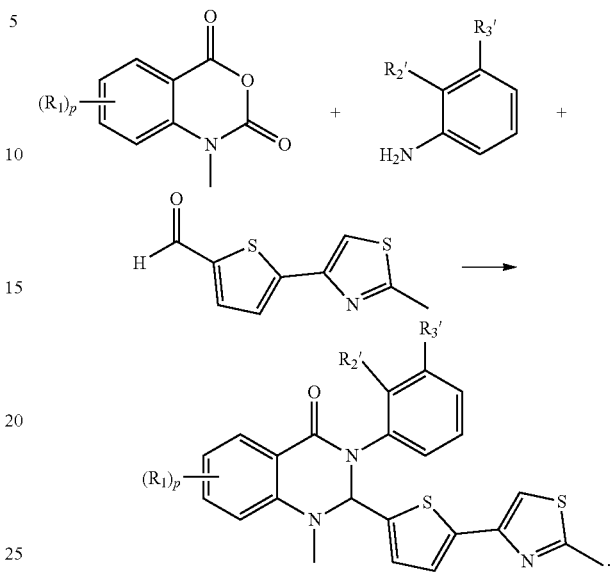

This reaction can in particular be carried out in an organic solvent.

According to an embodiment, the three starting compounds are mixed in an organic solvent, in particular acetic acid.

According to an embodiment, the organic solvent is heated, in particular under reflux or microwave irradiation, for example to a temperature of between 100° C. and 180° C., in particular from 110° C. to 140° C., more particularly from 120° C. to 130° C.

The heating time is from 10 minutes to 6 hours, for example from 30 minutes to 5 hours, in particular from 1 hour to 4 hours, more particularly from 2 to 3 hours.

$R_1$ and p are as defined above.

$R_2'$ and $R_3'$ correspond to the groups $R_2$ and $R_3$, respectively, or to adhoc protection groups.

According to an embodiment, $R_2'$ and $R_3'$ represent independently of each other a group selected from H, —OH, —$NO_2$, —$SO_2$—$NH_2$, on the condition that at least one of $R_2$ and $R_3$ does not represent H.

According to a particular embodiment, when $R_2'$ and/or $R_3'$ represent —$NO_2$, $R_2'$ and/or $R_3'$ are then converted into $R_2$ and/or $R_3$=—$NH_2$, in particular by one of the techniques well known to the person skilled in the art, for example by action of zinc in contact with acetic acid.

Definitions

As used in this description, the term "about" refers to a range of values of ±10% of a specific value. For example, the term "about 120 mg" includes values of 120 mg±10%, i.e. the values of 108 mg to 132 mg.

As used in this description, the percentages refer to percentages by weight of the total weight of the formulation, unless otherwise specified.

As used herein, the value ranges in the form of "x-y" or "from x to y" or "between x and y" include the limits x and y as well as the integers between these limits. For example, "1-5", or "from 1 to 5" or "between 1 and 5" refers to the integers 1, 2, 3, 4 and 5. The preferred embodiments include each individual integer within the range of values, as well as any sub-combination of those integers. For example, the preferred values for "1-5" may include the integers 1, 2, 3, 4, 5, 1-2, 1-3, 1-4, 1-5, 2-3, 2-4, 2-5, etc.

As used herein, the term "pharmaceutically acceptable salt" refers to salts that are, within the scope of a reasonable medical judgement, suitable for the contact with the human and animal tissues without excessive toxicity, irritation, allergic response, or other problematic complications commensurate with a reasonable benefit/risk ratio.

Pharmaceutically acceptable salts of the compounds of general formula (I) means the hydrochlorides, hydrobromides, sulphates or bisulphates, phosphates or hydrogen phosphates, acetates, oxalates, benzoates, succinates, fumarates, maleates, lactates, citrates, tartrates, gluconates, methanesulphonates, benzene sulphonates and paratoluene sulphonates.

Halogen atom means the chemical elements of the group VII of the periodic table of elements, in particular the fluorine, the chlorine, the bromine and the iodine.

The term alkyl radical with 1 to 3 or 4 carbon atoms designates a hydrogencarbon radical, linear or branched; examples include the methyl, the ethyl, the propyl, the isopropyl or the tertiobutyl.

By "PEG" or "poly(ethylene glycol)" or "polyethylene glycol" is meant in particular —$(CH_2—CH_2—O)_m$— groups, optionally terminated by a group selected from H, a $C_1$ to $C_3$ alkyl, or —$(—O—CH_2—CH_2)_m$— groups, optionally terminated by a group selected from H, —OH, and a O—$C_1$ to $C_3$ alkyl, m being selected from 1 to 500, in particular from 4 to 500, including from 30 to 60.

The average molar mass of the PEG may in particular be indicated after the term "PEG" after the name, for example PEG-1450 (1,450 g·mol$^{-1}$).

By "PLA" or "poly(lactic acid)" or "polylactic acid" is meant in particular —$(C(=O)—CH(CH_3)—O)_p$— groups, optionally terminated by a group selected from H, a $C_1$ to $C_3$ alkyl, or —$(O—CH(CH_3)—C(=O))_p$— groups, optionally terminated by a group selected from —OH, and a O—$C_1$ to $C_3$ alkyl, where p is selected from 1 to 2,000, in particular from 5 to 500, particularly from 10 to 50.

The average molar mass of the PLA may in particular be indicated after the term "PLA" after the name, for example PLA-1036 (1,036 g·mol$^{-1}$).

By "PLGA" or "PLG" is meant poly(lactic acid-co-glycolic acid), and in particular —$((C(=O)—CH(CH_3)—O)_p—(C(=O)—CH_2—O)_q)_r$— groups, optionally terminated by a group selected from H, a $C_1$ to $C_3$ alkyl, or —$((O—CH_2—C(=O))_q—(O—CH(CH_3)—C(=O))_p)_r$— groups, optionally terminated by a group selected from —OH and a O—$C_1$ to $C_3$ alkyl, p, q and r being such that the PLGA polymer is statistical or block, in particular statistical, and in particular such that the average molar mass of the PLGA, for example indicated after the term "PLGA" after the name, is between 200 and 4,000, in particular from 800 to 1,200 g·mol$^{-1}$. p, q and r are in particular such that the molar percentage of lactic acid in the PLGA is about 20%. In particular, p, q and r are such that the PLGA consists of 12 lactic acid units and 3 glycolic acid units.

EXAMPLES

Figure 1:
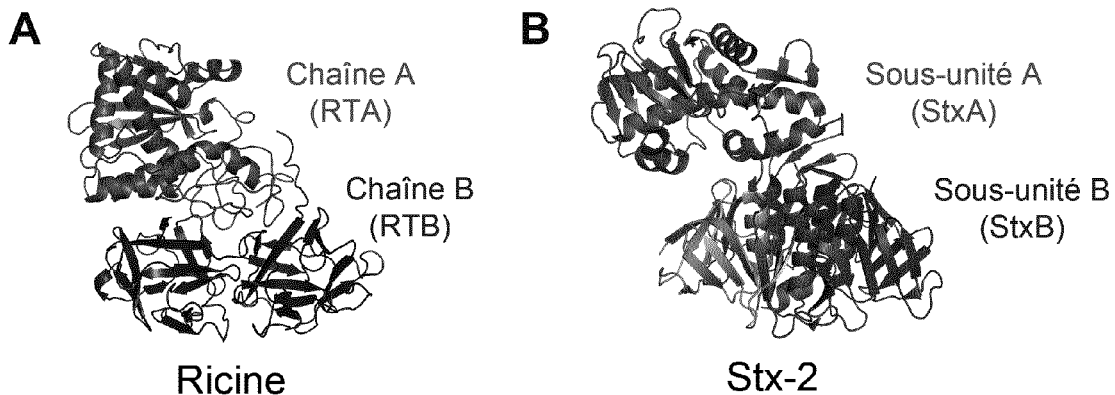
FIG. 1 shows the crystallographic structures of the ricin (A, whose name in the crystallographic structure database is pdb 2AAI) and the Stx2 (B, pdb 1R4P).
Figure 2:
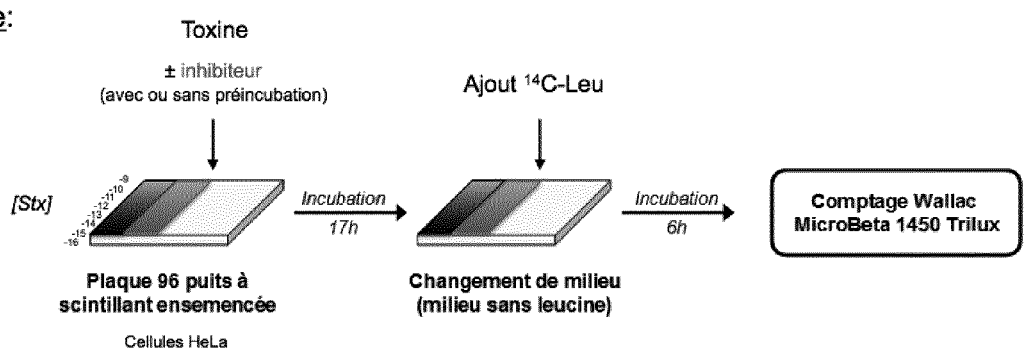
FIG. 2 is a schematic representation of the cell assay implemented in the experimental part.
Figure 2:
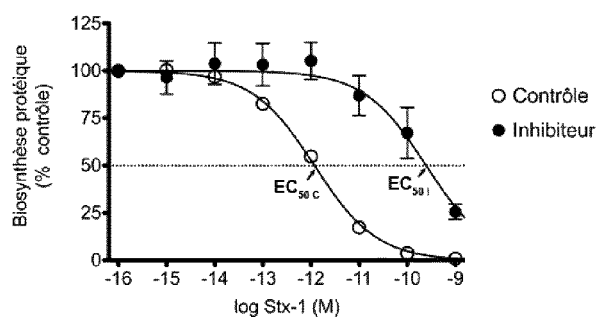
Figure 3:
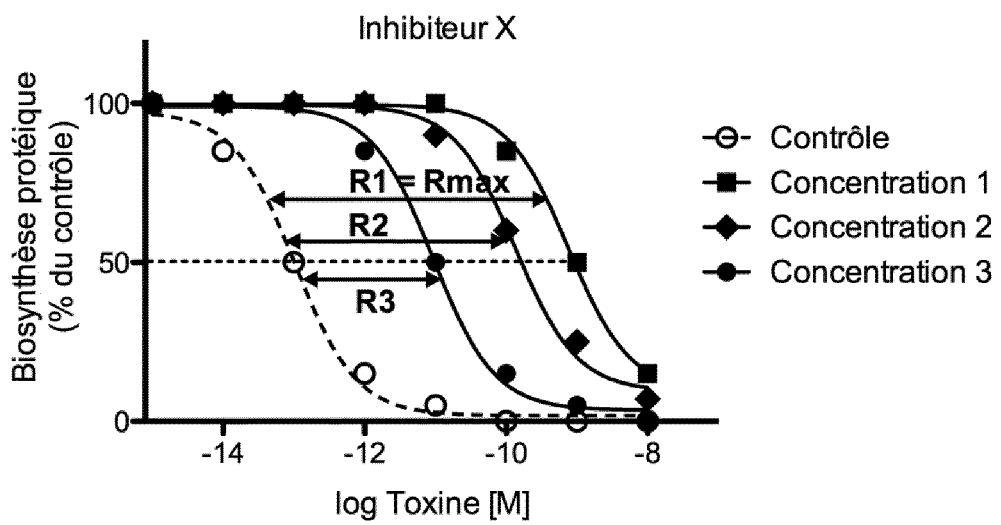
FIG. 3 illustrates the $IC_{50}$ calculation method performed in part II of the examples; the toxicity curves are performed in the absence of inhibitor (Control) and then in the presence of inhibitor at different concentrations.
Figure 3:
Figure 3:
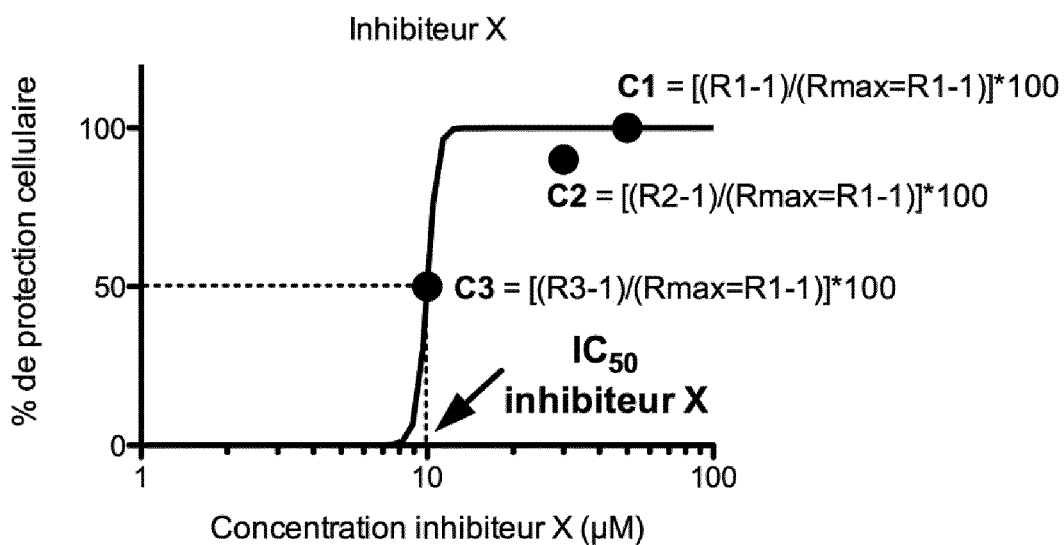

I. Synthesis of Compounds According to the Invention

All chemicals and solvents used in the syntheses are of reactive grade and were used without additional purification. The $CH_2Cl_2$ was distilled over calcium hydride before use. The glassware was flame dried under vacuum and cooled under nitrogen to room temperature. All the reactions were carried out under dry nitrogen and monitored by TLC.

In particular, the purification was performed on a CombiFlash with a UV-vis detector and RediSep columns. The samples were adsorbed onto the Celite or the silica and loaded into solid-filled cartridges. In particular, an ethyl acetate/cyclohexane or methanol/dichloromethane gradient was used. The fractions were in particular collected on the basis of a detection at 254 nm.

The analysis and the purification by HPLC-MS was carried out using a Waters system (binary gradient module 2525, in-line degasser, sample manager 2767, photodiode array detector 2996) with a binary system for the solvent gradient. In particular, the eluent was a gradient of (99.9% water/0.1% HCOOH) and (99.9% MeCN/0.1% HCOOH) or (99.9% water/0.1% HCOOH) and (99.9% MeOH/0.1% HCOOH). Each compound was deposited on a 100-4.6 mm (5 mm) Zorbax SB-C18 column equilibrated with $H_2O$/MeCN or $H_2O$/MeOH 95:5.

This system was for example coupled to a Waters Micromass ZQ system with a ZQ2000 quadrupole analyser. The ionisation was performed by electrospray and the other parameters were as follows: source temperature 120° C., cone voltage 20 V, and continuous sample injection at a flow rate of 0.3 mL per min. The mass spectra were recorded in positive and negative ion mode in the range m/z 100-2000 and processed with Mass Lynx 4.0 software.

The infrared spectra were in particular recorded on a Spectrum Two equipped with a UATR Two (Perkin Elmer), Diamond/ZnSe (1 reflection).

NMR analyses were in particular performed on a Bruker Avance 400 Ultrashield spectrometer. The 1H-NMR and 13C spectra were recorded at room temperature at 400 MHz and 100 MHz respectively, the samples were dissolved in DMSO-d6 or $CDCl_3$ at a concentration of approximately 5 mM. The DMSO singlet signal was set at 2.50 ppm. The chemical shifts are given in ppm and the coupling constants in Hz. The spectral data are consistent with the associated structures.

Preparation of the Compound 1

Synthesis of the Nitro Precursor 1'

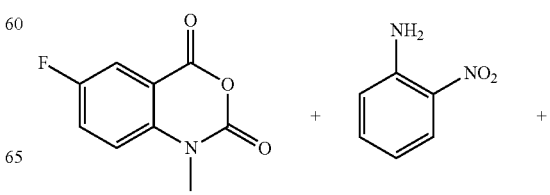

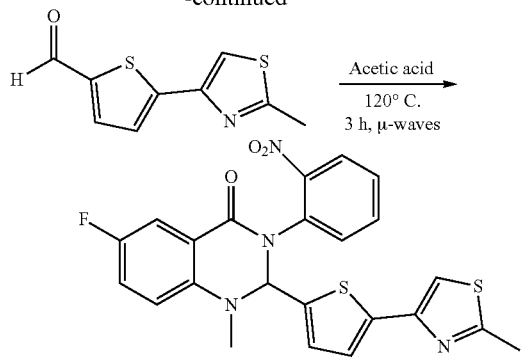

| Reagents | eq. | M (g/mol) | d | n (mmol) | m (mg) | V (mL) |
|---|---|---|---|---|---|---|
| 5-fluoro-N-methylisatoic anhydride | 1 | 195.15 | / | 1 | 195 | / |
| 2-nitroaniline | 1 | 138.13 | / | 1 | 138 | / |
| 5-(2-methyl-1,3-thiazol-4-yl)-2-thiophenecarbaldehyde | 1 | 209.00 | / | 1 | 209 | / |
| Acetic acid | / | / | / | / | / | 2 |

The mixture was stirred at 120° C. for 3 hours under microwave irradiation. The residue was dissolved in EtOAc and washed successively with a saturated solution of NaHCO₃ (three times), brine (twice) and water (once). The organic phase was dried on MgSO₄, filtered and concentrated. The residue was purified by chromatography (solid deposition), eluted by a mixture of cyclohexane/EtOAc: 9/1->1/1 (yield: 62%).

Synthesis of the Compound 1

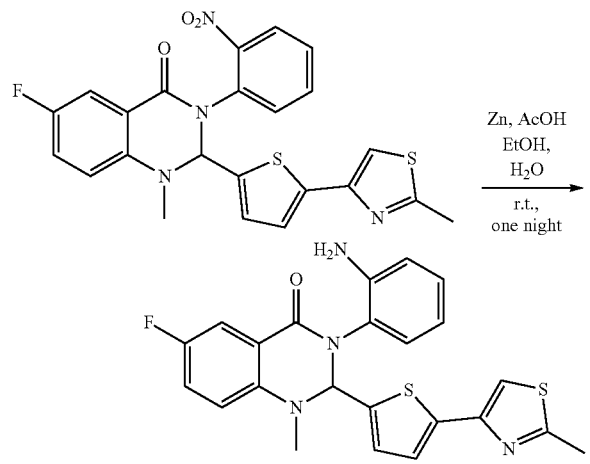

| Reagent | eq. | M (g/mol) | n (mmol) | m (mg) | V (mL) |
|---|---|---|---|---|---|
| 1' | 1 | 480.07 | 0.44 | 273 | / |
| Zn | 30 | 65.39 | 13.2 | 860 | / |
| EtOH | / | / | / | / | 10 |

| Reagent | eq. | M (g/mol) | n (mmol) | m (mg) | V (mL) |
|---|---|---|---|---|---|
| H₂O | / | / | / | / | 1.8 |
| AcOH | / | / | / | / | 0.9 |

The mixture was stirred overnight at room temperature, protected from light.

The residue obtained was purified by chromatography (solid deposit), eluted by a mixture of cyclohexane/EtOAc: 95/5->0/1, then re-precipitated by dissolving in the minimum of EtOAc and adding pentane (yield: 63%).

¹H NMR (CDCl₃): 2.69 (s, 3H); 2.91 (s, 3H); 4 (s broad, 2H); 5.76 (s, 1H); 6.54 (dd, 1H, J: 4, J: 8.9); 6.60 (td, 1H, J: 1.3, J: 7.8); 6.66 (d, 1H, J: 3.7); 6.75 (dd, 1H, J: 1.2, J: 8); 6.84 (dd, 1H, J: 1.4, J: 7.9); 7-7.1 (m, 3H); 7.1 (dd, 1H, J: 3.1, J: 8.7); 7.72 (dd, 1H, J: 3, J: 8.6).

¹³C NMR (CDCl₃): 19.1; 36; 76.2; 111.9; 114.4 (d, J: 7.1), 115.5 (d, J: 24); 116.7; 118.8 (d, J: 7.4); 118.9; 121.3 (d, J: 23.1); 122.7; 125.2; 128.3; 129.2; 129.5; 137.8; 138.6; 142; 143.1; 148.7; 156.6 (d, J: 239); 161; 166.4.

LC/MS: retention time: 3.23 min.

M+H.: 451.4.

Preparation of the Compound 2

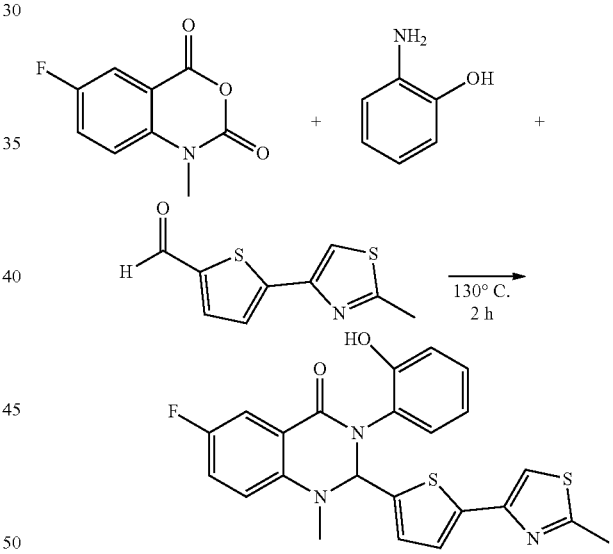

| Reagent | eq. | M (g/mol) | n (mmol) | m (mg) | V (mL) |
|---|---|---|---|---|---|
| 5-fluoro-N-methylisatoic anhydride | 1 | 195.03 | 1 | 195 | / |
| 2-aminophenol | 1 | 109.13 | 1 | 109 | / |
| 5-(2-methyl-1,3-thiazol-4-yl)-2-thiophenecarbaldehyde | 1 | 209.00 | 1 | 209 | / |
| Acetic acid | / | / | / | / | 2 |

The mixture was stirred at 130° C. for 2 hours. The residue was dissolved in EtOAc and washed successively with a saturated solution of NaHCO₃ (three times), brine (twice) and water (once). The organic phase was dried on MgSO₄, filtered and concentrated. The residue was purified by chromatography (solid deposition), eluted by a mixture of cyclohexane/EtOAc: 95/5->1/1, then re-precipitated by dissolving in minimum EtOAc and adding pentane (yield: 25%).

¹H NMR (DMSO-d6): 2.62 (s, 3H); 2.9 (s, 3H); 6.16 (s, 1H); 6.75 (td, 1H, J: 1.3, J: 7.7); 6.79 (dd, 1H, J: 4, J: 9); 6.93-7.01 (m, 3H); 7.15 (td, 1H, J: 1.7, J: 7.5); 7.28 (d, 1H, J: 3.6); 7.35 (td, 1H, J: 3.2, J: 8.8); 7.58 (dd, 1H, J: 3.1, J: 8.8); 7.71 (s, 1H).

¹³C NMR (DMSO-d6): 18.5; 35.5; 75.3; 112.7; 113.7 (d, J: 23.6); 115 (d, J: 7); 116.7; 117.8 (d, J: 7); 118.8; 121.1 (d, J: 23.1); 122.6; 126.2; 128.3; 128.7; 129.9; 137.6; 139; 143.3; 147.8; 152.6; 155.3 (d, J: 235); 159.5; 165.9

IR: 1646; 1496; 1450; 1163; 806; 740
LC/MS: retention time: 3.24 min.
M+H.: 452.4.

Preparation of the Compound 3

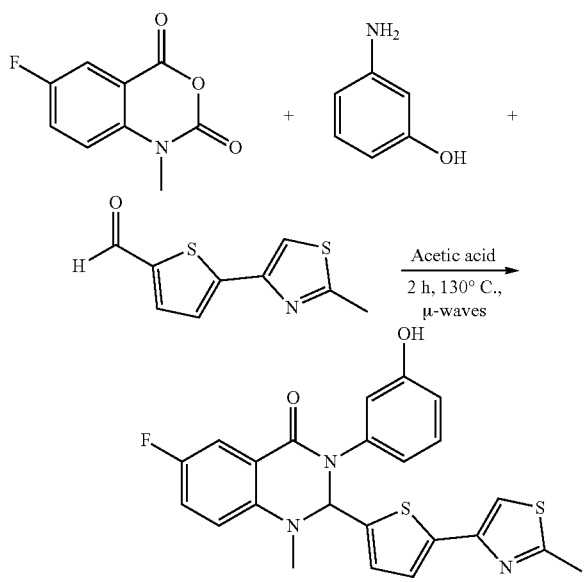

| Reagents | Formula | Molecular Mass | Mass (g) | Volume (mL) | n (mmol) |
|---|---|---|---|---|---|
| N-methyl-5-fluoroisatoic anhydride | C6H4FNO3 | 195.15 | 0.195 | / | 1.0 |
| 3-aminophenol | C6H7NO | 109.13 | 0.109 | / | 1.0 |
| 5-(2-methyl-1,3-thiazol-4-yl)-2-thiophenecarbaldehyde | C9H7NOS2 | 209.28 | 0.209 | / | 1.0 |
| Acetic acid | C2H4O2 | 60.05 | / | 2.00 | / |

The mixture was stirred at 130° C. for 2 hours. The residue was dissolved in EtOAc and the organic phase washed successively with a saturated NaHCO₃ solution and distilled water. The organic phase was dried on MgSO₄, filtered and concentrated under vacuum. The resulting brown solid was washed with a small amount of hot EtOAc to give a yellow powder (17%).

¹H NMR (DMSO-d6): 2.62 (s, 3H); 2.95 (s, 3H); 6.43 (s, 1H); 6.7-6.78 (m, 3H); 6.81 (dd, 1H, J: 4.2, J: 9); 6.97 (d, 1H, J: 3.7); 7.20 (t, 1H, J: 8); 7.33 (d, 1H, J: 3.6); 7.36 (dd, 1H, J: 3, J: 8.8); 7.61 (dd, 1H, J: 3, J: 8.8); 7.71 (s, 1H).

¹³C NMR (DMSO-d6): 18.5; 35.4; 76; 112.8; 113.7; 113.7 (d, J: 23); 114; 115.4 (d, J: 7); 116.8; 118 (d, J: 7); 121.3 (d, J: 23); 122.9; 128.2; 129.5; 137.7; 138.7; 140.8; 143.2; 147.7; 155.5 (d, J: 235); 157.6; 159.8; 166.

IR: 3161 (broad); 1612; 1499; 1452; 1187; 1156; 795; 766; 730.

LC/MS: retention time=3.16 min.
M+H.: 452.3.

The compound 7, of the following formula, is prepared analogously to compound 2 or 3.

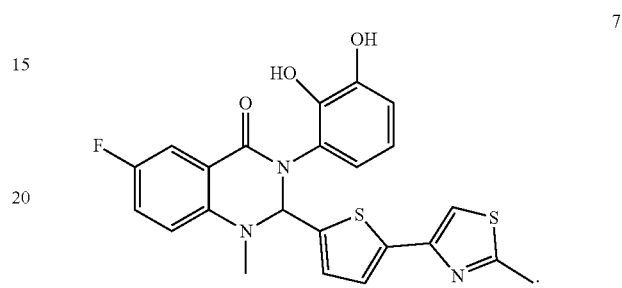

Preparation of the Compound 4

Synthesis of the Nitro Precursor 4'

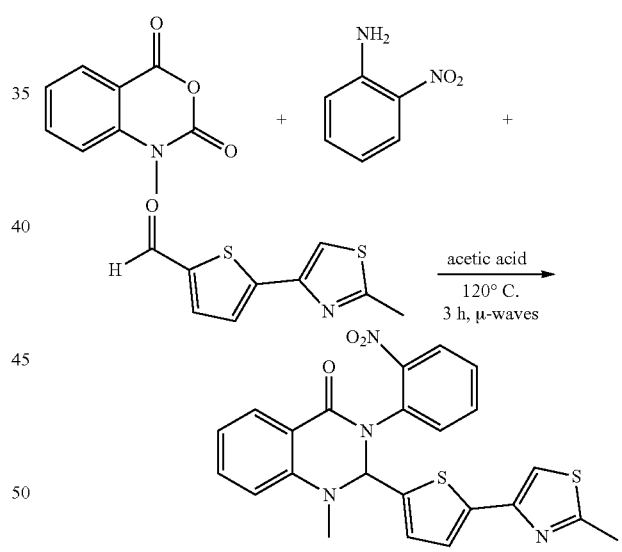

| Reagents | eq. | M (g/mol) | n (mmol) | m (mg) | V (mL) |
|---|---|---|---|---|---|
| N-methylisatoic anhydride | 1 | 177.04 | 1 | 177 | / |
| 2-nitroaniline | 1 | 138.13 | 1 | 138 | / |
| 5-(2-methyl-1,3-thiazol-4-yl)-2-thiophenecarbaldehyde | 1 | 209.00 | 1 | 209 | / |
| Acetic acid | / | / | / | / | 2 |

The mixture was stirred at 120° C. for 3 hours under microwave irradiation. The residue was dissolved in EtOAc and washed successively with a saturated solution of NaHCO₃ (three times), brine (twice) and water (once). The organic phase was dried on MgSO₄, filtered and concentrated under vacuum. The residue was purified by chromatography (solid deposition), eluted by a mixture of cyclohexane/EtOAc: 9/1->1/1 (yield: 49%).

Synthesis of the Compound 4

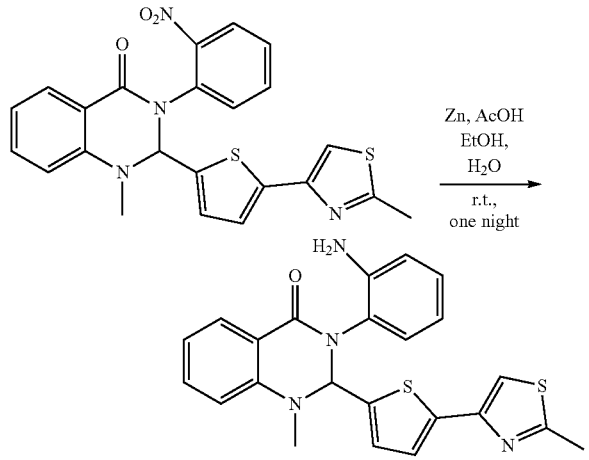

| Reagents | eq. | M (g/mol) | n (mmol) | m (mg) | V (mL) |
|---|---|---|---|---|---|
| 4' | 1 | 462.08 | 0.79 | 365 | / |
| Zn | 30 | 65.39 | 30 | 1500 | / |
| EtOH | / | / | / | / | 10 |
| H₂O | / | / | / | / | 1.8 |
| AcOH | / | / | / | / | 0.9 |

The mixture was stirred overnight at room temperature, protected from light.
The residue obtained was purified by chromatography (solid deposit), eluted by a mixture of cyclohexane/EtOAc: 95/5->0/1, then re-precipitated by dissolving in the minimum of EtOAc and adding pentane (yield: 81%).

¹H NMR (DMSO-d6): 2.62 (s, 3H); 2.90 (s, 3H); 5.04 (s, 2H); 5.97 (s, 1H); 6.48 (td, 1H, J: 1.2, J: 7.3); 6.68 (dd, 1H, J: 1.2, J: 7.7); 6.77 (d, 1H, J: 8.2); 6; 6.87 (dd, 1H, J: 1, J: 8); 6.9-6.96 (m, 2H); 7.03 (td, 1H, J: 1.3, J: 8.4); 7.3 (d, 1H, J: 3.6); 7.48 (td, 1H, J: 1.5, J: 8.6); 7.72 (s, 1H); 7.88 (dd, 1H, J: 1.5, J: 7.7).

¹³C NMR (DMSO-d6): 18.5; 34.9; 74.5; 112.7; 113; 115.9; 116.1; 117; 118.3; 122.6; 124.2; 128.1; 128.4; 128.7; 129.4; 134.2; 137.6; 138.7; 143.8; 143.8; 146.7; 147.8; 160.9; 165.9

LC/MS: retention time=3.18 min.
M+H.: 433.4.

Preparation of the Compound 5

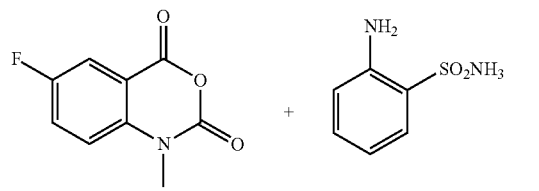

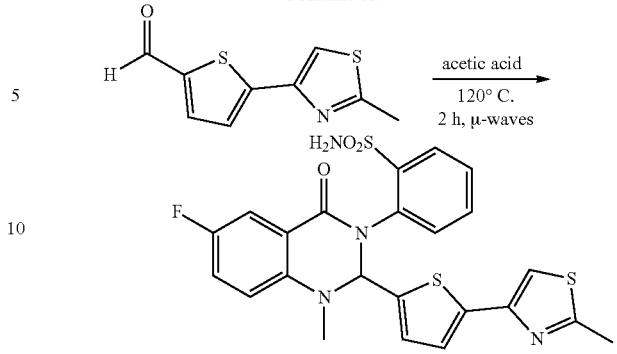

| Reagents | eq. | M (g/mol) | n (mmol) | m (mg) | V (mL) |
|---|---|---|---|---|---|
| 2-aminobenzenesulfonamide | 1 | 172.20 | 0.4 | 69 | / |
| 6-fluoro-N-methylisatoic anhydride | 1 | 195.03 | 0.4 | 78 | / |
| 5-(2-methyl-1,3-thiazol-4-yl)-2-thiophenecarbaldehyde | 1 | 209.28 | 0.4 | 84 | / |
| Acetic acid | / | / | / | / | 1 |

The mixture was stirred at 120° C. for 2 hours under microwave irradiation. The residue was dissolved in dichloromethane and washed successively with saturated NaHCO₃ solution (three times), brine (twice) and water (once). The organic phase was dried on MgSO₄, filtered and concentrated under vacuum. The residue was purified by chromatography (solid deposition), eluted by a mixture of cyclohexane/EtOAc: 9/1->0/1, then recrystallised in the dichloromethane (yield: 13%).

¹H NMR (DMSO-d6): 2.63 (s, 3H); 2.85 (s, 3H); 6.18 (s, 1H); 6.85 (dd, 1H, J: 4.2, J: 9.1)]; 6.89 (dd, 1H, J: 1.3, J: 7.4); 6.91 (d, 1H, J: 3.6); 7.32 (d, 1H, J: 7.6); 7.39 (td, 1H, J: 3.2, J: 8.7); 7.47 (s, 2H); 7.57-7.59 (m, 3H); 7.78 (s, 1H); 8.02 (dd, 1H, J: 1.9, J: 7.5).

¹³C NMR (DMSO-d6): 18.5; 35.24; 76.7; 113.09; 113.7 (J: 23.6) 114.9 (J: 7); 116.6 (J: 7); 121.6 (J: 22.9); 122.6; 128.3; 128.84; 129.4; 132.1; 132.5; 136.1; 137.6; 138; 141.2; 143.3; 147.7; 155.1 (J: 235); 160.4; 166.

IR: 3175; 1653; 1496; 1474; 1450; 1357; 1342; 1160; 821; 810; 710.

LC/MS: retention time=3.20 min.
M+H.: 515.4.

Preparation of the Compound 6 (Out-of-Invention)

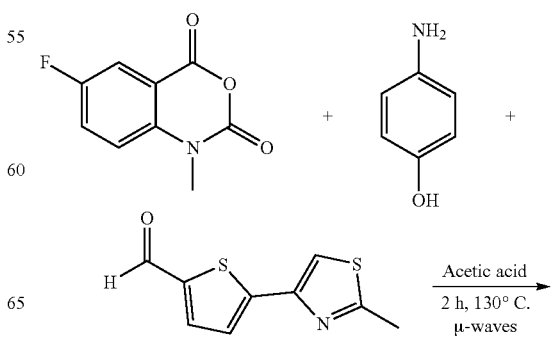

-continued

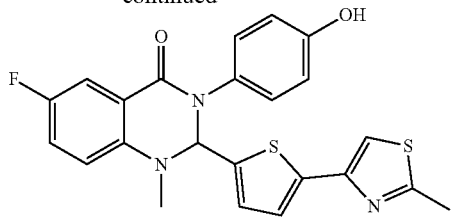

| Reagents | Formula | Molecular Mass | Mass (g) | Volume (mL) | n (mmol) |
|---|---|---|---|---|---|
| N-methyl-5-fluoroisatoic anhydride | C6H4FNO3 | 195.15 | 0.180 | / | 0.92 |
| 4-aminophenol | C6H7NO | 109.13 | 0.100 | / | 0.92 |
| 5-(2-methyl-1,3-thiazol-4-yl)-2-thiophenecarbaldehyde | C9H7NOS2 | 209.28 | 0.192 | / | 0.92 |
| Acetic acid | C2H4O2 | 60.05 | / | 2.00 | / |

The mixture was stirred at 130° C. for 2 hours under microwave irradiation. The residue was dissolved in ethyl acetate and the organic phase was washed successively with a saturated solution of $NaHCO_3$ and distilled water. The organic phase was dried on $MgSO_4$, filtered and concentrated under vacuum. The resulting brown solid was washed with a small amount of hot EtOAc to give a yellow powder (73%).

$^1$H NMR (DMSO-d6): 2.60 (s, 3H); 2.89 (s, 3H); 6.32 (s, 1H); 6.74-6.77 (m, 3H); 6.92 (wide s, 1H); 7.06 (d, 2H, J: 8.1); 7.3-7.35 (m, 2H); 7.57 (d, 1H, J: 6.6); 7.72 (s, 1H); 9.59 (s, 1H).

$^{13}$C NMR (DMSO-d6): 18.5; 35.3; 76.4; 112.8; 113.7 (J: 24); 115.2 (J: 7); 115.4; 117.9 (J: 7); 121.2 (J: 23); 122.8; 128; 128.4; 131; 137.7; 138.5; 143.3; 147.7; 155.5 (J: 235); 156.3; 159.9; 166.

IR: 3216 (broad); 1630; 1513; 1498; 1267; 1163; 888; 811; 737; 711.

LC/MS: retention time=3.33 min.
M+H.: 452.4.

II. Measurement to Evaluate the Protective Activity of the Compounds of the Invention Against the Shiga Toxin Protocol and Calculation of the $IC_{50}$ The compounds were tested in either A549 cells (human lung epithelial cells) or HeLa cells (human uterine cancer cells) against the Shiga toxin (Stx-1 and/or Stx-2). The human cells are grown at 37° C. in an atmosphere containing 5% $CO_2$ on 150 cm$^2$ culture flasks in DMEM (Dulbecco's Modified Eagle Medium) containing 100 U/mL of penicillin and 100 μg/mL of streptomycin. The cells are seeded at a density of 50,000 cells per well in plates of 96 Cytostar-T solid scintillation bottom wells (FIG. 2). The cells (100 μL in complete DMEM:DMEM+10% fetal calf serum, SVF) are pre-incubated or not with the inhibitors (50 μL; different concentrations, 3 h pre-incubation). Complete medium supplemented with toxin (50 μL, variable concentration range) is then added to each well. After a 20 h incubation, the medium (200 μL) is removed and replaced with leucine-free DMEM medium (Eurobio) containing 10% SVF and 0.5 μCi/mL of $^{14}$C-leucine (GE). After a 7 h incubation at 37° C., the incorporation of radioactivity by the cells is determined by reading the plates with a Wallac 1450 Microbeta trilux scintillation counter (PE).

As these toxins block the protein synthesis, the affected cells are no longer able to incorporate the radiolabelled leucine. In contrast, the cells treated with inhibitors still synthesise proteins and therefore incorporate the radiolabelled amino acid. As the cells concentrate the radioelement sufficiently close to the bottom of the well, this causes excitation of the scintillant contained in the plates and leads to photon emission detected by the scintillation counter (measured in counts per minute, cpm). This data is then expressed as a percentage of protein synthesis by the cells. The cytotoxicity curves can thus be plotted (FIG. 2) without inhibitor (white circles) or in the presence of an inhibitor (black circles). The analysis of the data by non-linear regression allows the $EC_{50}$ to be estimated, i.e. the effective concentration for which 50% uptake of radioactive leucine is observed, which corresponds to 50% of viable cells. The higher the $EC_{50}$ value, the greater the cell protection, as a higher concentration of toxin is required to generate the same cytotoxicity. It is thus possible to determine the effectiveness of the inhibitors by calculating the ratio R of the $EC_{50}$ (FIG. 2). The higher the value (>1), the greater the cell protection.

Six cytotoxicity curves are obtained in the absence and then in the presence of increasing concentrations of inhibitor. For each concentration (C) of inhibitor, a percentage of protection is determined from the value of R calculated by the Prism software with Rmax corresponding to the maximum value of R in the series:

$$\% \text{ protection} = [(R-1)/(R\max-1)]*100$$

The $IC_{50}$ is then calculated, using the Prism software by non-linear regression, from a graph where the corresponding percentage of cell protection is plotted for each compound concentration (see FIG. 3).

$IC_{50}$ corresponds to the concentration of compound giving 50% of its inhibiting power. The lower this concentration, the more powerful the inhibitor.

Results

| Compound | $IC_{50}$(nM) |
|---|---|
| Retro-2.1 (Control) | 100.0 |
| 4 | 78.6 |
| 1 | 14.2 |
| 2 | 20.0 |
| 3 | 55.0 |
| 5 | 35.0 |
| 7 | 41.0 |
| 6 (out-of-invention) | 483.0 |

The compound Retro-2.1 has the following formula:

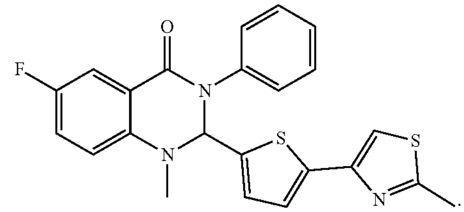 [SMILES: Cc1nc(-c2ccc(C3N(C)c4ccc(F)cc4C(=O)N3c3ccccc3)s2)cs1]

Conclusion

These results show that the tested compounds are all more potent inhibitors of the cellular effect of the Shiga toxin than the compound Retro-2.1 (out-of-invention control, in which the dihydroquinazolinone carries an unsubstituted phenyl), as well as the compound 6 (out-of-invention, in which the dihydroquinazolinone carries a phenyl substituted in the para position by a hydroxyl group).

III. Measure to Evaluate the Protective Activity of the Compounds of the Invention Against the Ricin The protocol and the calculation of the $IC_{50}$ of the compounds of the invention is similar to that presented in paragraph II, taking the ricin as toxin.

IV. Measurements to Evaluate the Protective Activity of the Compounds of the Invention Against Viruses Using Retrograde and/or Syntaxin 5-Dependent Transport, in Particular Viruses Entering the Cells by Endocytosis Cells as indicated below were seeded at a density of 50% in plates of 96 wells in a MEM medium supplemented with 10% of fetal bovine serum and incubated at 37° C., 5% of $CO_2$. The cells were allowed to stand overnight. The test compounds were dissolved in the DMSO at 20 mM each. The next day, each compound was diluted 100 times in MEM with serum, serially diluted (to 5 concentrations) and added in equal volume to the cell medium in each well. After 1 hour of pre-incubation, the virus was added at a multiplicity of infection (MOI) as indicated below. The viruses used comprise in particular recombinant viruses that encode a green fluorescent protein (Towner et al. 2005. Virology 332:20-7; or ANCHOR viruses supplied by NEO-VIRTECH). These viruses are capable of replication and exhibit a normal pathogenesis in animals. The cells were then fixed with 10% formalin for the time indicated below. The cell nuclei were stained with DAPI using standard methods. The infection was then analysed by photographing each well using an epifluorescent microscope. The total and infected cells were counted by counting DAPI-stained cells and green fluorescent cells respectively using Cell Profiler software. The fraction of infected cells was calculated by dividing the number of green fluorescent cells by the total number of cells. The evaluation of the $IC_{50}$ was performed as a function of the cell number using Combenefit software (Di Veroli et al. Bioinformatics 2016, 32(18), 2866-8).

Infection and fixation conditions:
MRC5 cells with hCMV-ANCHOR, MOI 1; fixation at 6 days;
HeLa cells with VACV-ANCHOR, MOI 0.1; fixation at 48 hours;
RK13 cells with Myxomavirus T1-ANCHOR, MOI 0.05; fixation at 6 days;
Hep2 cells with RSV; MOI 0.2; fixation at 72 hours.

Toxicity

Compound concentrations of the invention from 100 µM to 0.2 µM were tested (twice). The cells as described above were fixed 72 hours after addition of the compounds of the invention. The number of cells counted per well is normalized to the number of cells counted in the corresponding wells treated with DMSO only. The evaluation of the $CC_{50}$ was performed as a function of cell number using the Combenefit software mentioned above.

Results

The results obtained are reported in the following table:

| | | Retro-2.1 | 2 | 1 | 6 (out-of-invention) |
|---|---|---|---|---|---|
| HeLa/ VacV | CC50 (nM) | >50,000 | 32,300 | >50,000 | 20,400 |
| | CI50 (nM) | 37.8 | 3.61 | 1.05 | 628 |
| | Selectivity index | 1,323 | 8,947 | 47,619 | 32 |
| RK13/ MyxV T1 | CC50 (nM) | 3,350 | ND | 7,460 | 12,900 |
| | CI50 (nM) | 74.5 | 14.2 | 1.44 | 5,800 |
| | Selectivity index | 45 | ND | 5,181 | 2 |
| MRC5/ hCMV | CC50 (nM) | >50,000 | 21,000 | 21,500 | 16,700 |
| | CI50 (nM) | 11.6 | <1 | <1 | 281 |
| | Selectivity index | 4,310 | 21,000 | 21,500 | 59 |
| Hep2/ RSV | CC50 (nM) | >50,000 | 37,600 | >50,000 | 25,600 |
| | CI50 (nM) | 162 | 20 | ND | 2,200 |
| | Selectivity index | 309 | 1,880 | ND | 12 |

V. Measure to Evaluate the Protective Activity of the Compounds of the Invention Against a Bacteria Using the Retrograde and/or Syntaxin 5-Dependent Transport, in Particular a Bacteria Entering the Cells by Endocytosis HeLa229 cells are pre-treated with the compound of the invention to be evaluated at concentrations of 25.50 and 75 µM for 30 minutes until the bacteria is added to the cells.

The cells showing a primary infection are lysed 24 hours after the infection (hpi).

Cells treated with said compound are also lysed 48 h after the infection and the resulting lysate is used to infect new HeLa229 cells, which are lysed 24 h after the infection and analysed with the primary infection samples by immunoblot. The growth of the bacteria is detected using ad hoc antibodies and the actin is used as a control.

VI. Synthesis of Prodrugs According to the Invention

Prodrugs according to the present invention have been synthesized as follows:

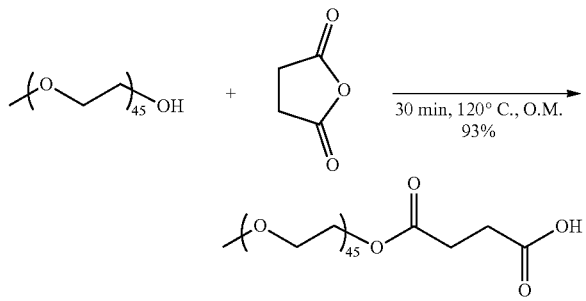

25
-continued

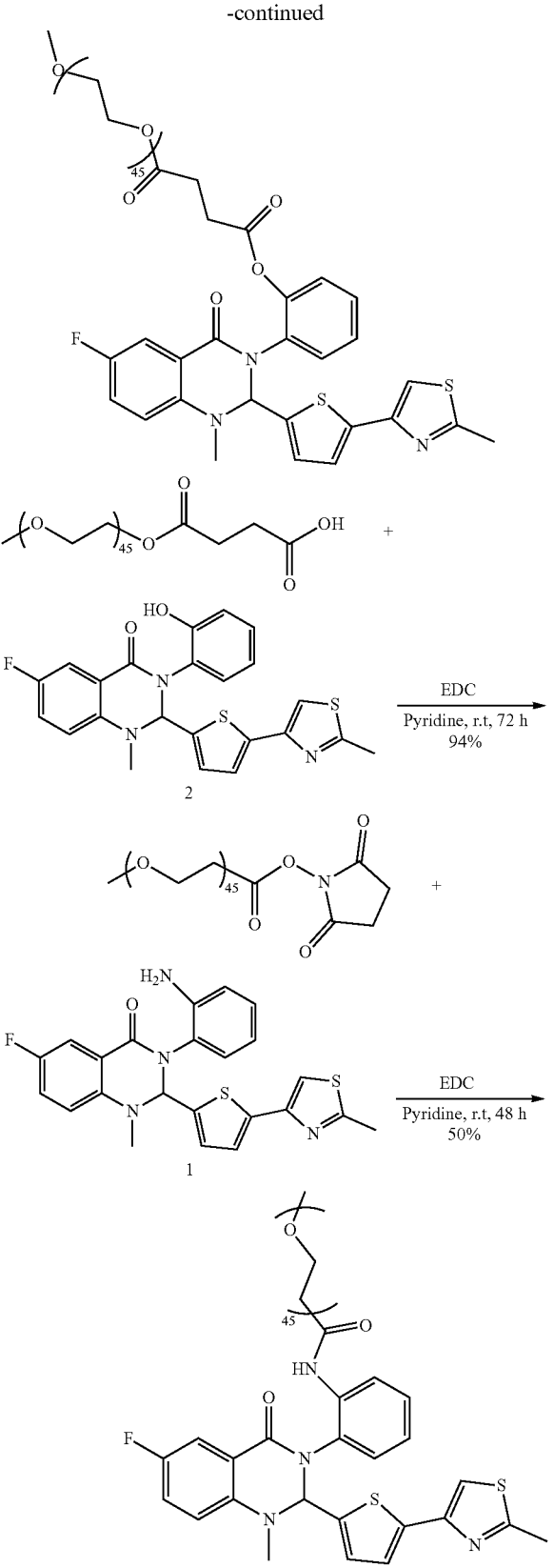

The compounds thus obtained have an excellent solubility in water (>700 mg/mL, possible administration in minipumps, infusion, i.v. injection). Their cleavage by the plasma amidases and/or esterases is rapid (e.g. with a $t_{1/2}$ of 2.6 hours in mouse plasma at 37° C.).

Other prodrugs, in the form of thermogelling polymers, have been obtained as follows:

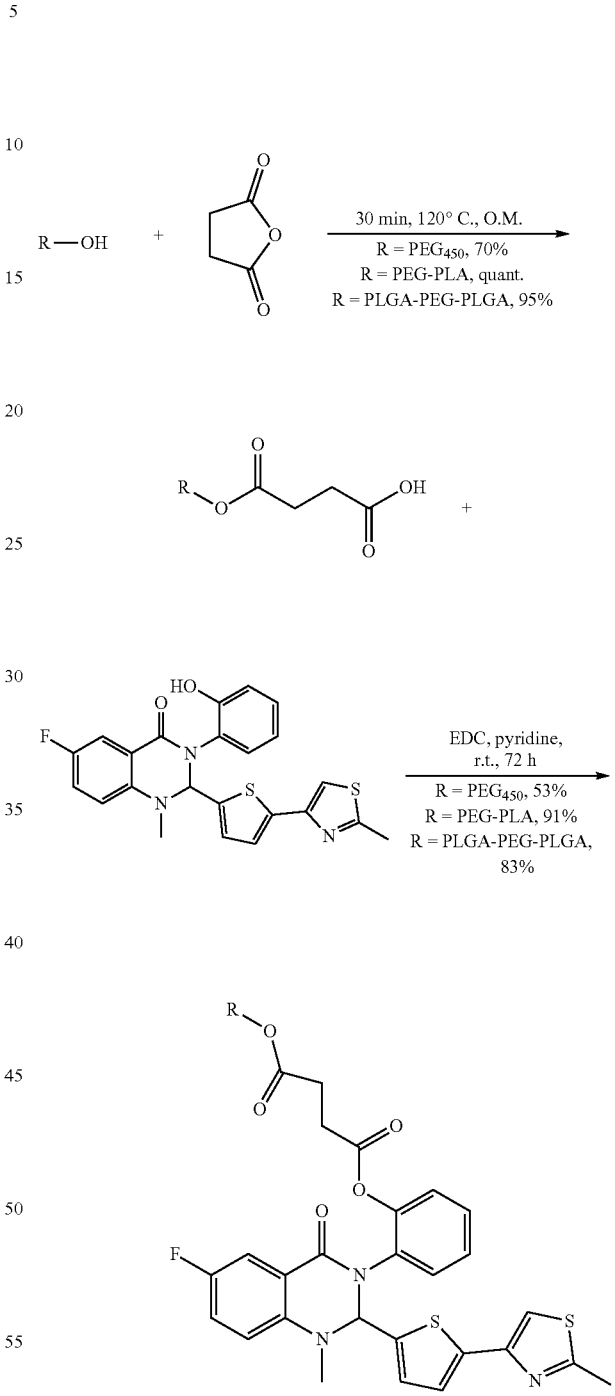

Or as follows:
(Compound 2)-PLGA1036-PEG1450-PLGA1036-(Compound 2) (Mn=4,393 g/mol) or
(Compound 2)-C(=O)—(CH₂)₂—C(=O)—PLGA1036-PEG1450-PLGA1036-C(=O)—(CH₂)₂—C(=O)-(Compound 2), in particular of the following formula:

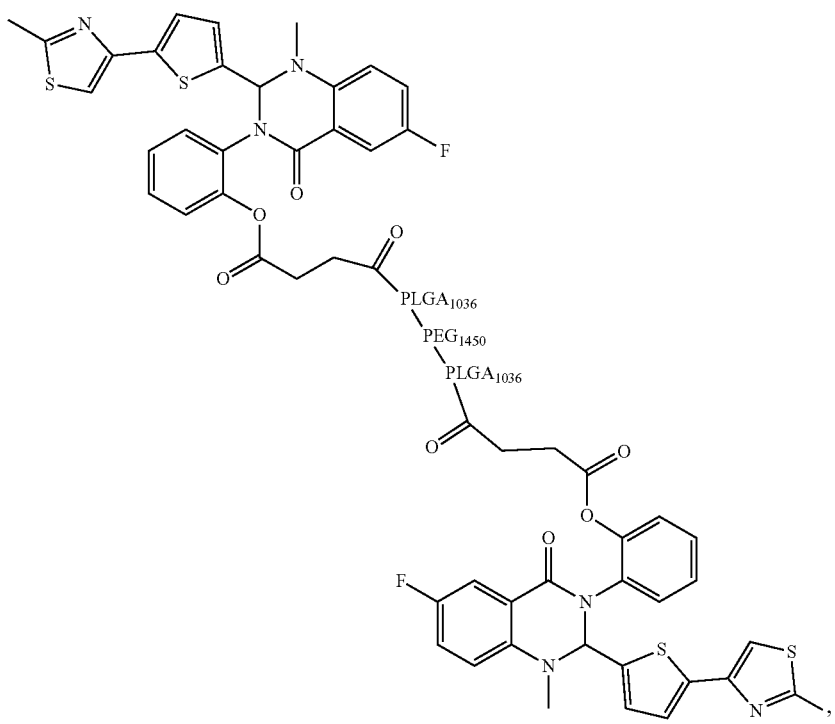

soluble in water and with thermogelation properties.

The PLGA1036-PEG1450-PLGA1036 is for example obtained as follows:

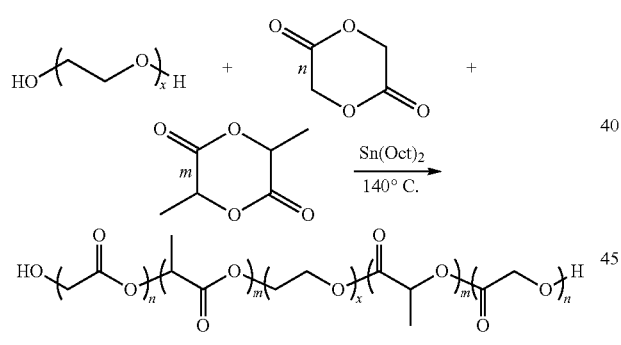

The poly(ethylene glycol) 1450 (3.00 g -2.07 mmol) is placed in a schlenk, heated to 100° C. in an oil bath. The schlenk is placed under vacuum for 2 h with stirring. The glycolide (0.6 g-5.13 mmol) and D,L-Lactide (2.64 g-18.3 mmol) were added to the schlenk and the mixture was heated to 130° C. until the solids were completely melted. The Sn(Oct)$_2$ (one drop) is added. The mixture is heated for 20 hours at 130° C. with stirring, under nitrogen. The mixture was brought to RT and dissolved in 20 mL of acetone. The solution is added drop by drop to distilled water at 4° C. with stirring. The mixture was stirred at 4° C. until the polymer was completely solubilised and then the mixture was heated to 80° C. The polymer is recovered by decantation. This sequence is repeated then the solid is dissolved in dichloromethane. The organic phase is dried on MgSO$_4$, filtered and evaporated to give a translucent gum which was dried under vacuum at 40° C. for 15 hours.

Purified product: 3.8 g (49%).

Molar mass (PLA)=1,707 g/mol; Molar mass (PGA)=365 g/mol, corresponding to a compound PLGA1036-PEG1450-PLGA1036 (Mn=3,522 g/mol; LA/GA=3.8).

The invention claimed is:

1. A compound of general formula (I):

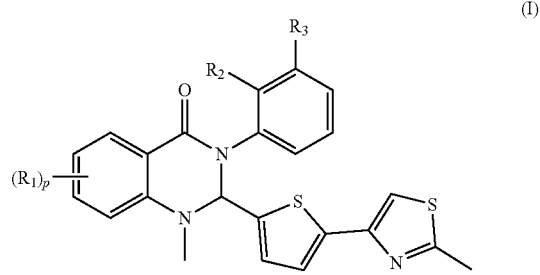

where:
p is equal to 1, 2 or 3;
R$_1$ represents on each occurrence, independently, a hydrogen atom, a halogen atom, an alkoxy radical of 1 to 3 carbon atoms;
R$_2$ and R$_3$ independently of each other represent a group selected from H, —OH, —OR$_4$, —NH$_2$, —NHR$_5$, —SO$_2$—NH$_2$, —SO$_2$—NH—R$_6$, on the condition that at least one of R$_2$ and R$_3$ does not represent H;
R$_4$, R$_5$ and R$_6$ independently of each other represent a group of formula (II) -L-(X)$_i$—(PEG)-(Y)$_j$—Z, wherein:
i and j independently of each other represent 0 or 1;
L represent —C(=O)— or —C(=O)—(CH$_2$)$_k$—C(=O)—, where k is 1, 2 or 3;
X and Y independently of each other represent a poly(lactic acid) or a poly(lactic acid-co-glycolic acid);

PEG represents a poly(ethylene glycol);

Z represents a group selected from H, a $C_1$ to $C_3$ alkyl, —OH, a O—$C_1$ to $C_3$ alkyl, or -L-$R_e$, wherein L is defined as above and $R_e$ is a residue of formula (I) linked to said -L-(X)$_i$—(PEG)-(Y)$_j$— group defined above via its $R_2$ or $R_3$ group, said $R_2$ or $R_3$ group being —OH, —$NH_2$ or —$SO_2$—$NH_2$;

as well or stereoisomers thereof or pharmaceutically acceptable salts thereof.

2. The compound of general formula (I) according to claim 1, wherein $R_3$ represents a hydrogen atom.

3. The compound of general formula (I) according to claim 1, wherein $R_2$ represents a hydrogen atom.

4. The compound of general formula (I) according to claim 1, wherein p is equal to 1.

5. The compound of general formula (I) according to claim 1, wherein $R_1$ represents a halogen atom.

6. The compound of general formula (I) according to claim 1, of the following formula (Ia):

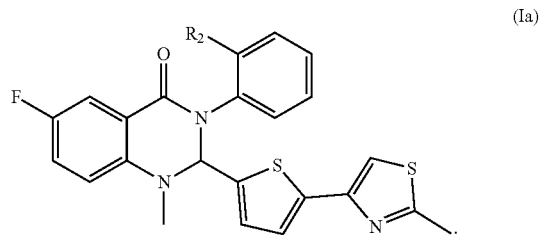

7. The compound of general formula (I) according to claim 1, selected from:

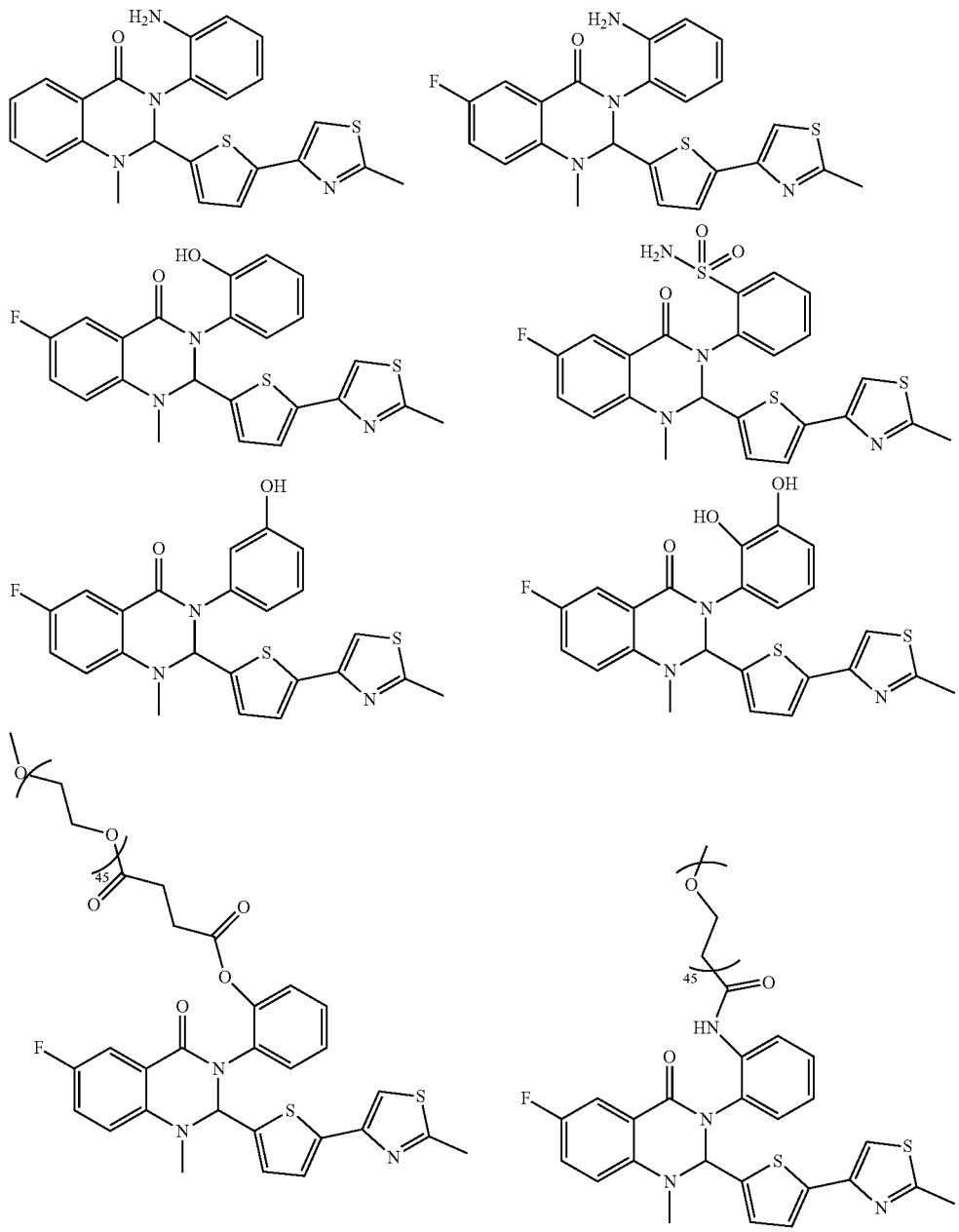

-continued

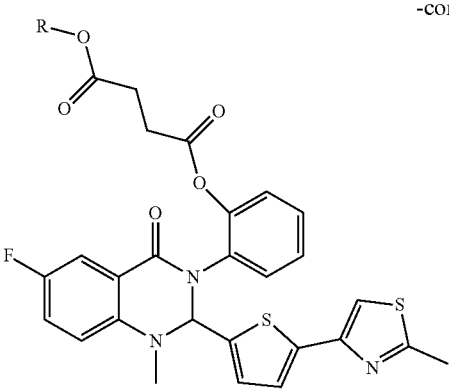

wherein R is selected from PEG450, PEG-PLA, PLGA-PEG-PLGA and PLGA$_{1036}$-PEG$_{1450}$-PLGA$_{1036}$, and

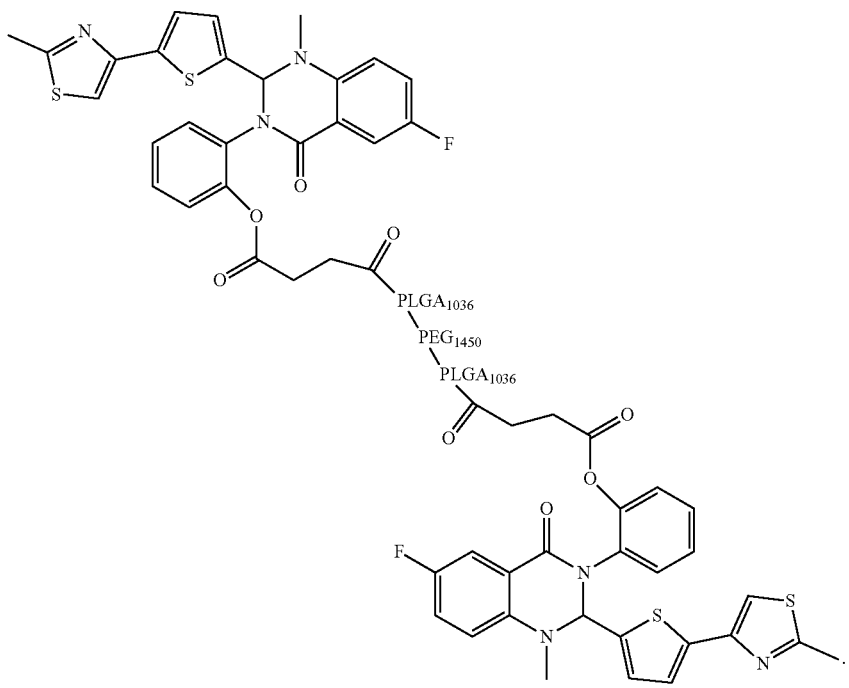

8. A pharmaceutical composition or medicament comprising at least one compound of general formula (I) as defined in claim 1 as active principle, and a pharmaceutically acceptable carrier, said pharmaceutical composition or said medicament being adapted for administration by the aerial, oral, parenteral or local routes.

9. The compound of general formula (I) according to claim 1, wherein R$_1$ is selected from the group consisting of: a methoxy group; —NO$_2$, and —NH$_2$.

10. The compound of general formula (I) according to claim 1, wherein k is 2.

11. The compound according to claim 5, wherein R$_1$ is a fluorine atom.

12. A method of treating a viral infection, comprising administering to a subject in need thereof the compound of general formula (I) according to claim 1.

13. A method of treating a bacterial infection, comprising administering to a subject in need thereof the compound of general formula (I) according to claim 1.

14. A method of treating a parasitic infection, comprising administering to a subject in need thereof the compound of general formula (I) according to claim 1.

15. A method of treating a viral infection according to claim 12, wherein the viral infection is caused by pox viruses, monkeypox virus, Vaccinia virus, leporipoxviruses, cytomegaloviruses, adeno-associated viruses, polyomaviruses, papillomaviruses, filoviruses, the Marburg virus, enteroviruses, herpes viruses, viruses of the genus *Arenavirus*, influenza viruses or pneumoviruses.

16. A method of treating a viral infection according to claim 15, wherein the virus is smallpox virus, myxomatosis virus, adeno-associated viruses of serotype 2, polyomavirus JC, polyomavirus BK, Ebola viruses, enterovirus 71, Herpes simplex virus of type 2, lymphocytic choriomeningitis virus, influenzaviruses A or respiratory syncytial virus.

17. A method of treating a bacterial infection according to claim 13, wherein the bacterial infection is caused by *Shigella dysenteriae, E. coli, Vibrio cholerae* or *Bordetella pertussis*.

* * * * *